US009886680B2

(12) United States Patent
Johnson et al.

(10) Patent No.: US 9,886,680 B2

(45) Date of Patent: Feb. 6, 2018

(54) LOW-POWER SIGNALING FOR MEDICAL DEVICES AND MEDICAL DEVICE PERSONNEL

(71) Applicant: ZOLL Medical Corporation, Chelmsford, MA (US)

(72) Inventors: Guy Robert Johnson, Gloucester, MA (US); Gary A. Freeman, Waltham, MA (US); Ulrich Herken, Medford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 15/076,085

(22) Filed: Mar. 21, 2016

(65) Prior Publication Data

US 2016/0283900 A1 Sep. 29, 2016

Related U.S. Application Data

(60) Provisional application No. 62/137,753, filed on Mar. 24, 2015.

(51) Int. Cl.

*G06Q 10/08* (2012.01)

*A61N 1/39* (2006.01)

(52) U.S. Cl.

CPC ............ *G06Q 10/087* (2013.01); *A61N 1/39* (2013.01); *A61N 1/3993* (2013.01)

(58) Field of Classification Search

CPC ....... A61N 1/39; A61N 1/3993; G06Q 10/087

USPC .................................................... 340/539.13

See application file for complete search history.

(56) References Cited

U.S. PATENT DOCUMENTS

2004/0024644 A1* 2/2004 Gui ........................ G06Q 10/08 705/22

2009/0124303 A1* 5/2009 Twitchell, Jr. ......... G06Q 10/08 455/574

2015/0220296 A1* 8/2015 Lin ....................... H04M 3/567 345/2.3

OTHER PUBLICATIONS

"Getting Started with iBeacon," Version 1.0, Apple, Jun. 2, 2014, (11 pages).

"Specification of the Bluetooth System, Master Table of Contents & Compliance Requirements," Covered Core Package Version 4.0, Jun. 30, 2010, vols. 1-6, Bluetooth SIG, (2302 pages).

"Specification of the Bluetooth System, Master Table of Contents & Compliance Requirements," Covered Core Package Version 4.1, Dec. 3, 2013, vols. 1-7, Bluetooth SIG, (2684 pages).

* cited by examiner

*Primary Examiner* — Nader Bolourchi

(74) *Attorney, Agent, or Firm* — Wilmer Cutler Pickering Hale and Dorr LLP

(57) ABSTRACT

Aspects of the present disclosure are directed toward apparatuses, systems, and methods that include at least one medical device having a device transceiver configured to wirelessly broadcast a device signal including at least unique identifier data and an information system is configured to maintain an active list of medical device inventory associated with a particular emergency response vehicle, and the processor is configured to automatically determine presence of the at least one medical device.

46 Claims, 3 Drawing Sheets

LOW-POWER SIGNALING FOR MEDICAL DEVICES AND MEDICAL DEVICE PERSONNEL

CROSS-REFERENCE TO RELATED APPLICATIONS

This application claims the benefit of U.S. Provisional Patent Application Ser. 62/137,753, filed on Mar. 24, 2015, entitled "Low-Power Signaling For Medical Devices and Medical Device Personnel," which is incorporated herein by reference in its entirety for all purposes.

TECHNICAL FIELD

The present invention relates to systems and methods for determining the location of one or more medical devices. More specifically, the present invention relates to systems and methods for determining a presence or location of multiple medical devices, and presenting the information regarding the presence of the medical devices on a user interface.

BACKGROUND

Medical devices used in emergency medical service (EMS) applications or emergency response situations, for example, defibrillators, are typically complex and expensive. The presence and/or locations of such devices are typically tracked and inventoried manually (for example, verbally or via an electronic log). Thus, it may be cumbersome to efficiently track and locate medical devices in certain situations, such as mass casualty situations.

Further, medical devices can include wireless data transceivers to transmit medical information for storage in a remote medical database. However, some designs lack relatively long-range communication components (such as cellular or Wi-Fi transceivers) and in some situations, such as mass casualty situations, relatively long-range communication methods may be unavailable. In these cases, some medical devices may turn to relatively short-range, device-to-device communication methods (such as near-field communications (NFC), Bluetooth, and the like) to transmit information.

SUMMARY

A system according to embodiments of the present disclosure including at least one medical device having a device transceiver configured to wirelessly broadcast a device signal including at least unique identifier data; and an information system comprising a system transceiver, at least one display device, at least one processor, and at least one database, wherein the information system is configured to maintain an active list of medical device inventory associated with a particular emergency response vehicle, and the processor is configured to automatically determine presence of the at least one medical device in response to the system transceiver receiving the device signal, and provide an indication on the at least one display device if the at least one medical device is present.

A system according to embodiments of the present disclosure including at least one medical device having a device transceiver configured to wirelessly broadcast a device signal including at least unique identifier data; and an information system comprising a system transceiver, at least one display device, at least one processor, and at least one database, wherein the information system is configured to maintain an active list of medical device inventory associated with a particular emergency response vehicle, and the processor is configured to automatically determine presence of the at least one medical device in response to the system transceiver receiving the device signal, measure a signal strength of the device signal and determine whether the at least one medical device is in one of at least three location-based conditions in response thereto, and provide an indication on the at least one display device if the at least one medical device is present and the location-based condition of the at least one medical device.

A system according to embodiments of the present disclosure including at least one medical device having a device transceiver configured to wirelessly broadcast a device signal including at least unique identifier data; and an information system comprising a system transceiver, at least one display device, at least one processor, and at least one database, wherein the information system is configured to maintain an active list of medical devices associated with a particular emergency response situation, and the processor is configured to automatically determine presence of the at least one medical device in response to the system transceiver receiving the device signal, and provide an indication on the at least one display device if the at least one medical device is present.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
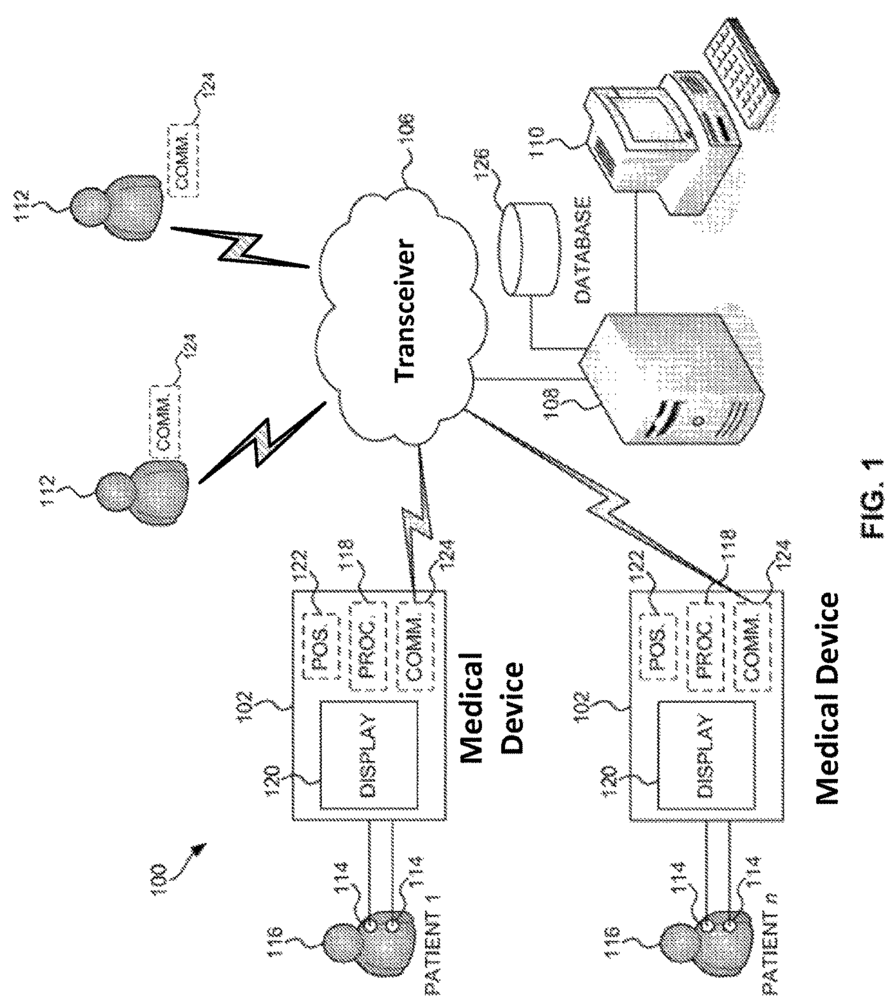
FIG. 1 illustrates a system for determining the presence of one or more medical devices, consistent with various aspects of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 illustrates a system 100 for determining the presence of one or more medical devices 102. The medical devices 102 can be used in connection with a particular emergency response vehicle or a particular emergency response situation. The medical devices 102 wirelessly transmit and communicate data using, for example, low-power Bluetooth, near-field communications (NFC), WiFi, cellular, ZigBee radio, and the like, to an information system 108 (e.g., hand-held device, tablet, smart phone, laptop computer, desktop computer) via a system transceiver 106.

The medical devices 102 can receive signals from one or more sensors or electrodes 114 coupled to the patient 116. In some embodiments, a processor 118 uses such signals to monitor, detect, and/or derive or calculate various patient conditions. For example, the processor 118 may monitor, detect, and/or derive or calculate heart rate, blood pressure, temperature, respiration rate, blood oxygen level, end-tidal carbon dioxide level, pulmonary function, blood glucose level, and/or weight. In some embodiments, the medical device 102 includes a display 120 for presenting data associated with one or more of the above medical parameters. For example, the display 120 may present an electrocardiograph (ECG).

The medical devices 102 may be, for example, defibrillators (such as ZOLL® X-Series® or E-Series® devices), automatic external defibrillators (AEDs, such as ZOLL® AED Pro® devices), wearable cardioverter defibrillators (such as ZOLL® LifeVest® devices), combinations thereof, and the like. Some of the medical devices 102 may be assigned to patients (that is, currently connected to patients and gathering data), and some of the medical devices 102 may be unassigned (that is, currently disconnected from patients and not gathering data). For simplicity, the following paragraphs only provide the details for one assigned medical device 102. It is to be understood, however, that in some embodiments similar details apply to each of the different types of devices 102.

The medical device 102 receives signals from one or more sensors or electrodes 114 coupled to the patient 116. In some embodiments, a processor 118 uses such signals to monitor, detect, and/or derive or calculate various patient conditions. For example, the processor 118 may monitor, detect, and/or derive or calculate heart rate, blood pressure, temperature, respiration rate, blood oxygen level, end-tidal carbon dioxide level, pulmonary function, blood glucose level, and/or weight. In some embodiments, the medical device 102 includes a display 120 for presenting data associated with one or more of the above medical parameters. For example, the display 120 may present an electrocardiograph (ECG).

A transceiver 124 is provided with each of the medical devices 102 to wirelessly transmit and communicate a device signal that includes the above noted data. The transceiver 124 can be provided integrally with the medical devices 102, or the transceiver 124 may be removable. The device signal can include a short message having a universally unique identified (UUID), that is associated with a given one of the medical devices 102, a Major Identifier, Minor Indenter and/or data indicative of a power (signal strength) calibration value. The calibration value is a stored value that indicates specific distances the transceiver 124 is away from the information system 108 based on the power or signal strength. This calibration value can be provided by measuring various distances (one foot, two feet, three feet) the transceiver 124 is away from the information system 108, noting the power or signal strength at those points, and storing the association between the power or signal strength value and the various distances. In this manner, the spacial location of the transceiver 124 can be determined with respect to its distance from the information system 108. The transceiver 124, when associated with the medical devices 102, is referred to as a device transceiver. Further, in embodiments where the transceiver 124 is provided as part of a device, the processor of the medical device 102 is configured to wirelessly broadcast the device signal on a regular basis. The device signal can also include stored device information (for example, the device's type, model number, serial number, device capabilities, assigned setting, such as an ambulance or hospital, and the like) and/or associated patient information (that is, information about the patient 116 to which the medical device 102 is assigned) to the information system 108 via the system transceiver 106. Such patient information may include, for example, the patient's name, age, weight, height, medical history, past and/or real-time medical data obtained by the medical device 102, and the like. In some embodiments, the system 100 may use the ZOLL® RescueNet® Link system to transmit medical data obtained by the medical devices 102 to the information system 108.

The UUID can be a 16 byte string used to differentiate a large group of related medical devices 102. For example, all Automatic External Defibrillators from the same manufacturer would use the same UUID. This allows the information system 108 identify the medical devices 102 used to identify AED's. The major identifier can be a 2 byte string used to distinguish a subset of medical devices 102 within the larger group. The minor identifier can be a 2 byte string meant to identify an individual medical device 102. The data indicative of a power can be used to determine a proximity (distance) the medical device 102 is from the information system 108. The data indicative of power is defined as the strength of the signal a known distance (for example, a meter, two meters, or three meters) between the medical device 102 and the information system 108. This value is recorded, and the information system 108 uses this power as a baseline to give a rough distance estimate.

In certain embodiments, as discussed in further detail below, a transceiver 124, consistent with various aspects of the present disclosure, can be provided with a medical device personnel 112 (or crew member) and wirelessly broadcast a crew signal to the information system 108. In these embodiments, the transceiver 124 may be a standalone device, or can be provided as part of, for example, a smart watch, smart phone, or tablet that is carried by or on the medical device personnel 112. Further, in embodiments where the transceiver 124 is provided as part of a device, the device's processor is configured to wirelessly broadcast the crew signal on a regular basis. In instances where the transceiver 124 is provided as a standalone device, the standalone device also includes a processor that is configured to wirelessly broadcast the crew signal on a regular basis. Similar to the medical devices 102, the transceiver 124 provided with the medical device personnel 112 carries the crew signal with a short message having a universally unique identified (UUID), that is associated with the medical device personnel 112, a Major Identifier, Minor Indenter and/or data indicative of a power (signal strength) calibration value. The calibration value is a stored value that indicates specific distances the transceiver 124 is away from the information system 108 based on the power or signal strength. This calibration value can be provided by measuring various distances (one foot, two feet, three feet) the transceiver 124 is away from the information system 108, noting the power or signal strength at those points, and storing the association between the power or signal strength value and the various distances. In this manner, the spacial location of the transceiver 124 can be determined with respect to its distance from the information system 108. The transceiver 124, when associated with the medical device personnel 112, is referred to as a mobile transceiver.

A database 126 in communication with the information system 108 stores device information (for example, device types, model numbers, serial numbers, device capabilities, assigned setting, and the like). More specifically, the database 126 stores information that includes an active list of medical device inventory associated with the particular emergency response vehicle or particular emergency response situation. The information system 108 associates the data wirelessly transmitted by one or more of the medical devices 102 with information about one or more of the medical devices 102 that is stored in the database 126. Similarly, in some embodiments the database 126 (or another database) stores information about one or more medical device personnel 112. The information system 108 associates the data wirelessly transmitted by the transceiver 124 associated with one or more medical device personnel 112 with information about one or more medical device personnel 112 that is stored in the database 126. In addition, the database 126 can store data related to a storage capacity of an emergency response vehicle, and data indicative of a storage location of the active list of medical device inventory within the emergency response vehicle.

In response to the system transceiver 106 receiving the device signal (or crew signal), the information system 108 automatically determines the presence of the medical devices 102. In certain embodiments, the information system 108 measures a signal strength of the device signal (or crew signal), and determines whether the associated medical device 102 is in one of at least three location-based conditions. In addition, the information system 108 provides an indication on the at least one display device 110 if the medical device 102 is present. In embodiments where the location-based condition is measured, the information system 108 also provides an indication of the location-based condition on the display device 110. The data wirelessly transmitted the medical devices 102 is unique to that device. Thus, the information system 108 is configured to automatically determine the presence of more than one of the medical devices 102 in response to receiving the associated the device signal. In these instances, the information system 108 provides an indication on the display device 110 if the information system 108 senses that the medical device 102 is present. In certain embodiments, the information system 108 is configured to scan for known transceivers 124. In addition, if the transceiver 124 is sensed, the information system 108 logs the contact event in the database 126.

As noted above, the information system 108 is configured to automatically determine the presence of more than one medical device 102 and/or more than one medical device personnel 112 based in response to the system transceiver 106 receiving an associated device signal or crew signal. In these instances, the information system 108 is configured to provide an indication on the at least one display device 110 if the more of the medical devices 102 and/or medical device personnel 112 are present. More specifically, the display device 110 displays data indicative of each medical devices 102 and/or each medical device personnel 112 if the information system 108 senses the associated device signal or crew signal.

The embodiments discussed herein may also be considered as methods as operated and/or executing by the system discussed consistent with various aspects of the present disclosure.

Figure 2:
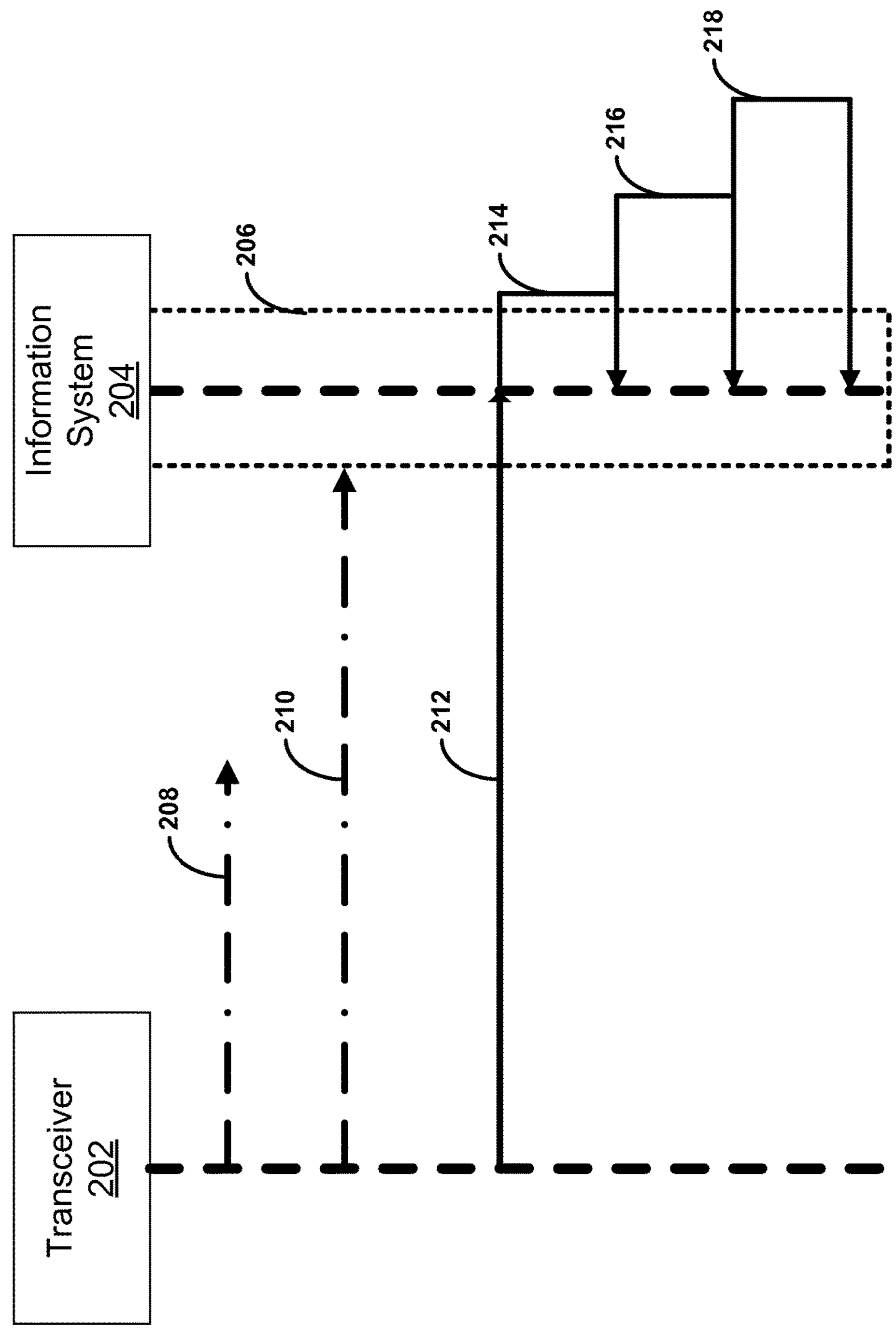
FIG. 2 illustrates an example communication and detection of a transceiver carried with a medical device or by a medical device personnel, consistent with various aspects of the present disclosure.

FIG. 2 illustrates an example communication and detection of a transceiver 202 carried with a medical device or by a medical device personnel, consistent with various aspects of the present disclosure. As noted above in connection with FIG. 1, the transceiver 202 communicates a data signal (208/210/212) that is detected by an information system 204. The information system 204 (system transceiver not shown) has a range 206 in which the data signal (208/210/212) is sensed. For instance, the data signal (208/210/212) is shown in three different strengths. The first strength 208 lies outside the range 206 of the information system 204, the second strength 210 touches or is adjacent to the range 206 of the information system 204, and the third signal strength 212 is within the range 206 of the information system 204. In instances where the transceiver 202 communicates at the first strength 208, the presence of the transceiver 202 (and its associated medical device or medical device personnel) will not be sensed by the information system 204 as the transceiver 202 is out of range 206 of the information system 204. In instances where the transceiver 202 communicates at the second strength 208, the presence of the transceiver 202 (and its associated medical device or medical device personnel) is sensed by the information system 204, but the data/information carried by the transceiver 202 is not within the range 206 of the information system 204 such that the data/information can be read and/or stored by the information system 204. In instances where the transceiver 202 communicates at the third strength 210, the presence of the transceiver 202 (and its associated medical device or medical device personnel) is sensed by the information system 204, and the data/information carried by the transceiver 202 can be read and/or stored by the information system 204.

In response to the information system 204 sensing the presence of the transceiver 202 communicating at the third strength 210, the data/information carried by the transceiver 202 can be read 214 against by the information system 204 against a database stored therein. As noted above, the information system 204 can include a database that stores an active list of medical device inventory associated with an emergency response vehicle or emergency response situation. In other embodiments, the information system 204 can include a second database that stores an active list of medical device personnel associated with an emergency response vehicle or emergency response situation. The information system 204 also logs 216 that the data/information carried by the transceiver 202 has been read 214 by the information system 204. This allows for the information system 204 to track which medical devices or medical device personnel are present. Further, the information system 204 also provides an alert on 218 (on a user interface) indicating presence of one or more medical devices and/or medical device personnel in response to sensing the presence of the transceiver 202 associated with one or more medical devices or medical device personnel. Further, the information system 108 can indicate, on the display 120, the inventory information, which can be verified by a user (such as a crew member for the emergency response vehicle or emergency response situation), who can verify that all medical devices 102 are reloaded before leaving a scene.

In certain embodiments, based on sensing the relative strength of the data signal (208/210/212), such as the device signal or crew signal, broadcast by the transceiver 202, the information system 204 can automatically determine a spacial locations the transceiver 202 and its associated medical device or medical device personnel. In addition, the information system 204 (via its processor) can provide an alert on a display device indicating that the associated medical device or medical device personnel is present. Further, the information system 204 provides an indication that the medical device or medical device personnel is missing in response to the data signal (208/210/212), such as the device signal or crew signal, being out of range of the information system 204.

Figure 3:
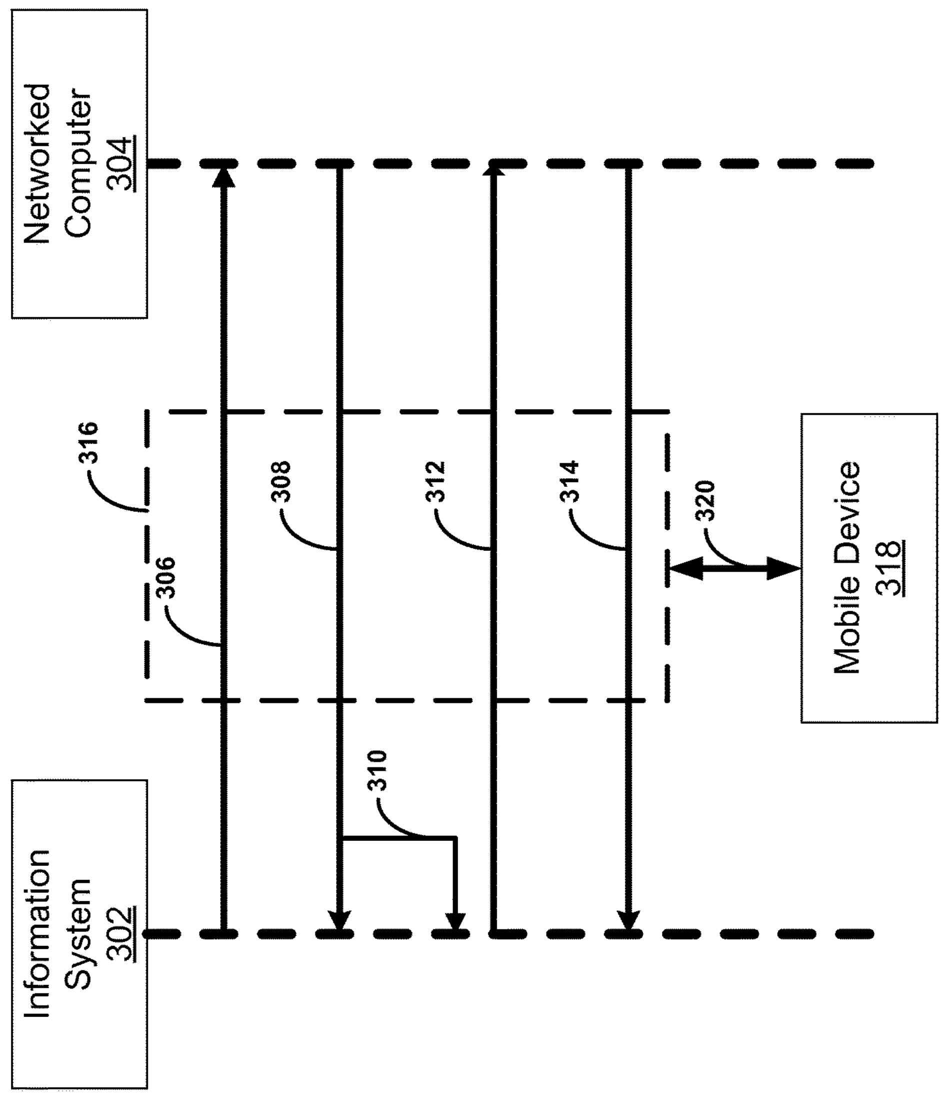
FIG. 3 illustrates an example communication between an information system and a networked computer, consistent with various aspects of the present disclosure.

In certain embodiments, the information system 204 is configured to measure a signal strength of the data signal (208/210/212), such as a device signal or crew signal, and determine as broadcast by the transceiver 202 and its associated medical device or medical device personnel. In these embodiments, the information system 204 determines whether the at least one medical device or medical device personnel is in one of at least three location-based conditions in response thereto. As noted above, the data signal (208/210/212) indicates that whether the transceiver 202 lies outside the range 206 of the information system 204 (first strength 208), the transceiver touches or is adjacent to the range 206 of the information system 204 (second strength 210), or the transceiver 202 is within the range 206 of the information system 204 (third signal strength 212). In such an embodiment, the information system 204 provides an indication on its display device if the at least one medical device or medical device personnel is present, and the location-based condition of the at least one medical device or medical device personnel. The display can provide the location-based condition indicating as whether the transceiver 202 lies outside the range 206 of the information system 204 (first strength 208), the transceiver 202 is in a pairing condition (third signal strength 212), or whether the transceiver 202 can be sensed, but is not close enough to be paired (e.g., an intermediate condition). In certain embodiments, FIG. 3 illustrates an example communication between an information system 302 and a networked computer 304, consistent with various aspects of the present disclosure. As discussed above, the information system 302 is configured to communicate with one or medical devices and/or medical device beacons based on receiving low-power signals broadcast by a transceiver. The information system 302, in certain embodiments, can also wirelessly communicate with the networked computer 304 in order to exchange data, or offload data for detailed computations. For instance, the information system 302 can include an internal database, as described above, and the networked computer 304 can also include a database. Each database can store data indicative of a storage capacity of an emergency response vehicle (or emergency response situation), and data indicative of a storage location of the active list of medical device inventory within the emergency response vehicle (or emergency response situation).

In certain embodiments, the information system 302 wirelessly communicates 306 a current active inventory list of medical devices or medical device personnel to the networked computer 304. The networked computer 304 can, as prompted by the information system 302 or a user at the networked computer 304, communicate 308 an updated inventory list of medical devices or medical device personnel to the information system 302. The information system 302 will compare 310 the current active inventory list of medical devices or medical device personnel to the list transmitted by the networked computer 304, and update the active list of inventory as necessary. The information system 302 can then communicate the changes in inventor back 312 to the networked computer 304. Further, the networked computer 304 can communicate an acknowledgement 314 that the information system 302 has the correct inventory of medical devices or medical device personnel stored thereon.

In certain embodiments, the networked computer 304 and the networked computer 304 communicate via a cloud-based server 316. In these embodiments, the cloud-based server 316 can also include a database that stores the communicated messages, and related inventory information. The cloud-based server 316 can enable communication 320 with at least one mobile device 318. In addition, the cloud-based server 316 can enable communication with other devices or computers. Further, the cloud-based server 316 allows for communication of inventory information across multiple systems. For instance, medical devices may be part of the same inventory that is accessed by more than one information system 302. As a result, the inventory can be tracked based on which information system 302 is uses a certain medical device. Further, more than one networked computer 304 may be provided. Each networked computer 304 may communicate with another networked computer 304 using peer-to-peer networking.

In certain embodiments, the networked computer 304 may monitor the information collected by the information system 302, as described in detail above. In this manner, the networked computer 304 may communicate with another networked computer 304 and transfer monitoring responsibilities therebetween.

As noted above, in certain embodiments, the cloud-based server 316 can be accessed by at least one mobile device 318. The mobile device 318 can include various mobile applications that interact with the information system 302. For instance, the cloud-based server 316 can store the data collected by the information system 302, and a mobile application run by the mobile device 318 queries the cloud-based server 316 with information regarding a specific medical device or medical device personnel (equipped with the above noted transceiver). In this manner, the mobile device 318 is able to confirm the location of the specific medical device or medical device personnel, the status of the specific medical device or medical device personnel, or other related information. Further, a user of the mobile device 318 can add a picture of the GPS location or inventory location of a medical device or medical device personnel, which can be communicated to the cloud-based server 316. The cloud-base server 316 can then associate this picture data with the associated medical device or medical device personnel. Such location-based GPS information can also be associated, by the mobile device 318, with other travel service applications (e.g. WAZE, GARMIN) or other beacon-type applications.

The mobile application provided with the mobile device 318 can incorporate other applications. For instance, the mobile application can provide CPR instruction, CPR compression depth and rate when possible if the networked medical device, communicating through the cloud-based server, includes the interactive capabilities (e.g., an AED equipped with CPR data capabilities). Further, the mobile application can be automatically communicate with a medical device, to obtain treatment data. The mobile application can upload this data to the cloud-based server 316, which can be relayed to an EMS service or medical device personnel. The mobile application can incorporate other modules to assess patient; e.g. use microphone to analyze heart sound or breathing sounds.

The cloud-based server 316 can also provide the mobile device 318 with access to the system via an installer mobile application that allows the mobile device 318 to be trusted/verified. The mobile device 318 can then receive information regarding various medical devices such as the device location model, manufacturer, battery type, service interval, contact information, EMS contact information. The mobile application can also query the cloud-based server 316 in information mode and location information will be provided. Further, in an emergency response situation, a mobile application can query the cloud-based server 316 in emergency mode signaling a medical emergency. During a medical emergency the cloud-based server 316 can notify other mobile application users of the medical emergency and the need for a particular medical device (such as an AED). Responding mobile app users will be supplied with location and navigation information to retrieve closest AED and transport it to user making the request. More that one user can be notified to locate and transport an AED to the user reporting the medical emergency.

In certain embodiments, the cloud-based server 316 can notify a mobile application user of possible maintenance need and readiness check when a medical device is requested. When available server will periodically query the medical device via the cloud-based server 316 for readiness status and update records as needed. Thus, the cloud-based server 316 tracks possible need for medical device service. In this manner, when the medical device has been serviced, a user having the mobile application can update the cloud-based server 316. Further, if a medical device is requested and closest medical device has outstanding service need associated with it, the cloud-based server 316 can provide alternate locations.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. A system comprising:

at least one medical device having a device transceiver configured to wirelessly broadcast a device signal including at least unique identifier data; and an information system comprising a system transceiver, at least one display device, at least one processor, and at least one database, wherein the information system is configured to maintain an active list of medical device inventory associated with a particular emergency response vehicle, and the at least one processor is configured to:

automatically determine presence of the at least one medical device in response to the system transceiver receiving the device signal;

measure a signal strength of the device signal and determine whether the at least one medical device is in one of at least three location-based conditions in response thereto, wherein the at least three location-based conditions include an out-of-range condition, a pairing condition, and an intermediate condition;

provide an indication on the at least one display device if the at least one medical device is present and the location-based condition of the at least one medical device; and provide an indication on the at least one display device when the at least one medical device transitions between one or more of the at least three location-based conditions.

2. The system of claim 1, further comprising at least one mobile transceiver arranged with at least one member of a crew for a particular emergency response vehicle and configured to wirelessly broadcast a crew signal that includes unique identifier data.

3. The system of claim 2, wherein the at least one processor is further configured to measure a signal strength of the crew signal and determine if the at least one member of the crew is in one of at least three location-based conditions in response thereto.

4. The system of claim 3, wherein the at least one processor is further configured to provide an alert on the at least one display device indicating the spatial location of the at least one member of the crew relative to the spatial location of the at least one medical device.

5. The system of claim 2, wherein the at least one mobile transceiver is provided with a smart watch, smart phone, or tablet.

6. The system of claim 1, wherein the information system is a hand-held device.

7. The system of claim 1, wherein the at least one medical device is at least one of a defibrillator, an automatic external defibrillator, and a wearable cardioverter defibrillator.

8. The system of claim 2, wherein the at least one processor is further configured to automatically determine spatial locations of the at least one medical device and the at least one member of the crew with respect to the information system.

9. The system of claim 1, wherein the at least one processor is further configured to measure the signal strength of the device signal to determine a spatial location of the at least one medical device.

10. The system of claim 1, wherein the at least one processor is further configured to provide an alert on the at least one display device indicating the at least one medical device is missing in response to the system transceiver not receiving the device signal.

11. The system of claim 1, wherein the at least one medical device includes a plurality of medical devices each having a device transceiver configured to wirelessly broadcast an associated device signal, each device signal having unique identifier data, and wherein each of the plurality of medical devices are on the active list of medical device inventory.

12. The system of claim 11, wherein the at least one processor is further configured to:

automatically determine presence of at least one of the plurality of medical devices in response to the system transceiver receiving one or more of the plurality of associated device signals; and provide an indication on the at least one display device if at least one of the plurality of medical devices is present.

13. The system of claim 12, wherein each of the plurality of associated device signals includes device identifier data and other data unique to each of the plurality of medical devices.

14. The system of claim 12, further comprising at least one mobile transceiver arranged with at least one member of a crew for a particular emergency response vehicle configured to wirelessly broadcast a crew signal that includes crew identifier data, and wherein the at least one processor is configured to display the active list of medical device inventory on the at least one display device in response to the system transceiver receiving the crew signal.

15. The system of claim 1, wherein the at least one database includes data indicative of a storage capacity of the emergency response vehicle, and data indicative of a storage location of the active list of medical device inventory within the emergency response vehicle.

16. A system comprising:

a plurality of medical devices each having transceivers configured to wirelessly broadcast a plurality of associated device signals having unique identifier data; and an information system comprising a system transceiver, at least one display device, at least one processor, and at least a first and a second database, wherein the information system is configured to:

maintain an active list of medical devices associated with a particular emergency response situation; and maintain an active list of crew responding to the emergency response situation; and the at least one processor is configured to:

automatically determine presence of at least one medical device of the plurality of medical devices in response to the system transceiver receiving one of the plurality of device signals;

provide an indication on the at least one display device if the at least one medical device is present;

update the active list of medical devices in response to the system transceiver receiving the plurality of associated device signals, wherein the plurality of associated device signals include device identifier data and other data unique to each of the plurality of medical devices;

store the updated active list of medical devices within the first or second database;

update the active list of crew responding to the emergency response situation in response to the system transceiver receiving a crew signal; and store the updated active list of crew within the second database; and at least one mobile transceiver arranged with at least one member of the crew responding to the emergency response situation and configured to wirelessly broadcast the crew signal that includes crew identifier data.

17. The system of claim 16, wherein the at least one medical device is at least one of a defibrillator, an automatic external defibrillator, and a wearable cardioverter defibrillator.

18. The system of claim 16, wherein the at least one processor is further configured to measure a signal strength of the device signal and determine whether the at least one medical device is in one of at least three location-based conditions in response thereto, wherein the at least three location-based conditions include an out-of-range condition, a pairing condition, and an intermediate condition.

19. The system of claim 18, wherein the at least one processor is further configured to provide an indication on the at least one display when the at least one medical device transitions between one or more of the at least three location-based conditions.

20. The system of claim 16, wherein the at least one processor is further configured to measure a signal strength of the crew signal and determine if the at least one member of the crew is in one of at least three location-based conditions in response thereto.

21. The system of claim 20, wherein the at least one processor is further configured to provide an alert on the at least one display device indicating the spatial location of the at least one member of the crew relative to the spatial location of the at least one medical device.

22. The system of claim 16, wherein the at least one mobile transceiver is provided with a smart watch, smart phone, or tablet.

23. The system of claim 16, wherein the information system is a hand-held device.

24. A system comprising:

a plurality of medical devices each having transceivers configured to wirelessly broadcast a plurality of associated device signals having unique identifier data;

a plurality of transceivers associated with crew members and configured to wirelessly broadcast a plurality of associated crew signals having unique identifier data; and an information system comprising a system transceiver, at least one display device, at least one processor, and at least a first and a second database, wherein the information system is configured to maintain an active list of medical devices associated with a particular emergency response situation, and the at least one processor is configured to:

automatically determine presence of at least one of the plurality of medical devices in response to the system transceiver receiving one of the plurality of device signals;

provide an indication on the at least one display device if the at least one medical device is present;

update the active list of medical devices in response to the system transceiver receiving the plurality of associated device signals, wherein the plurality of associated device signals include device identifier data and other data unique to each of the plurality of medical devices;

store the updated active list of medical devices within the first or second database;

update the active list of crew responding to the emergency response situation in response to the system transceiver receiving a crew signal; and store the updated active list of crew within the second database; and at least one mobile transceiver arranged with at least one member of the crew responding to the emergency response situation and configured to wirelessly broadcast the crew signal that includes crew identifier data.

25. The system of claim 24, wherein the at least one medical device is at least one of a defibrillator, an automatic external defibrillator, and a wearable cardioverter defibrillator.

26. The system of claim 24, wherein the at least one processor is further configured to measure a signal strength of the device signal and determine whether the at least one medical device is in one of at least three location-based conditions in response thereto, wherein the at least three location-based conditions include an out-of-range condition, a pairing condition, and an intermediate condition.

27. The system of claim 26, wherein the at least one processor is further configured to provide an indication on the at least one display device when the at least one medical device transitions between one or more of the at least three location-based conditions.

28. The system of claim 24, wherein the at least one processor is further configured to measure a signal strength of the crew signal and determine if the at least one member of the crew is in one of at least three location-based conditions in response thereto.

29. The system of claim 28, wherein the at least one processor is further configured to provide an alert on the at least one display device indicating the spatial location of the at least one member of the crew relative to the spatial location of the at least one medical device.

30. The system of claim 24, wherein the at least one mobile transceiver is provided with a smart watch, smart phone, or tablet.

31. The system of claim 24, wherein the information system is a hand-held device.

32. A system comprising:

at least one medical device having a device transceiver configured to wirelessly broadcast a device signal including at least unique identifier data;

at least one mobile transceiver arranged with at least one member of a crew for a particular emergency response vehicle and configured to wirelessly broadcast a crew signal that includes unique identifier data; and an information system comprising a system transceiver, at least one display device, at least one processor, and at least one database, wherein the information system is configured to maintain an active list of medical device inventory associated with the particular emergency response vehicle, and the at least one processor is configured to:

automatically determine presence of the at least one medical device in response to the system transceiver receiving the device signal;

measure a signal strength of the device signal and determine whether the at least one medical device is in one of at least three location-based conditions in response thereto, wherein the at least three location-based conditions include an out-of-range condition, a pairing condition, and an intermediate condition; and provide an indication on the at least one display device if the at least one medical device is present and the location-based condition of the at least one medical device.

33. The system of claim 32, wherein the at least one processor is further configured to provide an indication on the at least one display device when the at least one medical device transitions between one or more of the at least three location-based conditions.

34. The system of claim 32, wherein the at least one processor is further configured to measure a signal strength of the crew signal and determine if the at least one member of the crew is in one of at least three location-based conditions in response thereto.

35. The system of claim 34, wherein the at least one processor is further configured to provide an alert on the at least one display device indicating the spatial location of the at least one member of the crew relative to the spatial location of the at least one medical device.

36. The system of claim 32, wherein the at least one mobile transceiver is provided with a smart watch, smart phone, or tablet.

37. The system of claim 32, wherein the information system is a hand-held device.

38. The system of claim 32, wherein the at least one medical device is at least one of a defibrillator, an automatic external defibrillator, and a wearable cardioverter defibrillator.

39. The system of claim 32, wherein the at least one processor is further configured to automatically determine spatial locations of the at least one medical device and the at least one member of the crew with respect to the information system.

40. The system of claim 32, wherein the at least one processor is further configured to measure the signal strength of the device signal to determine a spatial location of the at least one medical device.

41. The system of claim 32, wherein the at least one processor is further configured to provide an alert on the at least one display device indicating the at least one medical device is missing in response to the system transceiver not receiving the device signal.

42. The system of claim 32, wherein the at least one medical device includes a plurality of medical devices each having a device transceiver configured to wirelessly broadcast an associated device signal, each device signal having unique identifier data, and wherein each of the plurality of medical devices are on the active list of medical device inventory.

43. The system of claim 42, wherein the at least one processor is further configured to:

automatically determine presence of at least one of the plurality of medical devices in response to the system transceiver receiving one or more of the plurality of associated device signals; and provide an indication on the at least one display device if at least one of the plurality of medical devices is present.

44. The system of claim 43, wherein each of the plurality of associated device signals includes device identifier data and other data unique to each of the plurality of medical devices.

45. The system of claim 43, further comprising at least one mobile transceiver arranged with at least one member of a crew for a particular emergency response vehicle configured to wirelessly broadcast a crew signal that includes crew identifier data, and wherein the at least one processor is configured to display the active list of medical device inventory on the at least one display device in response to the system transceiver receiving the crew signal.

46. The system of claim 32, wherein the at least one database includes data indicative of a storage capacity of the emergency response vehicle, and data indicative of a storage location of the active list of medical device inventory within the emergency response vehicle.

* * * * *